United States Patent
Johnson (10) Patent No.: US 12,029,397 B2
(45) Date of Patent: Jul. 9, 2024

(54) SAMPLE COLLECTION KIT INCLUDING CAP HAVING SELECTIVELY OPENABLE DIAPHRAGM VALVE

(71) Applicant: SPECTRUM SOLUTIONS, LLC, Draper, UT (US)

(72) Inventor: Neil Jeremy Johnson, Riverton, UT (US)

(73) Assignee: Spectrum Solutions L.L.C., Draper, UT (US)

( * ) Notice: Subject to any disclaimer, the term of this patent is extended or adjusted under 35 U.S.C. 154(b) by 947 days.

(21) Appl. No.: 17/028,617

(22) Filed: Sep. 22, 2020

(65) Prior Publication Data

US 2021/0085296 A1 Mar. 25, 2021

Related U.S. Application Data

(60) Provisional application No. 62/904,080, filed on Sep. 23, 2019.

(51) Int. Cl.
*A61B 10/00* (2006.01)
*B01L 3/00* (2006.01)

(52) U.S. Cl.
CPC .......... *A61B 10/0051* (2013.01); *B01L 3/502* (2013.01); *A61B 2010/009* (2013.01)

(58) Field of Classification Search
CPC ....... B01L 2300/0072; B01L 2300/044; B01L 3/502; A61B 10/0051; A61B 2010/009
See application file for complete search history.

(56) References Cited

U.S. PATENT DOCUMENTS

| D287,570 S | 1/1987 | Olsen |
| D310,264 S | 8/1990 | Leoncavallo et al. |

(Continued)

FOREIGN PATENT DOCUMENTS

| CA | 2721263 A1 | 10/2009 |
| CN | 105173361 A | 12/2015 |

(Continued)

OTHER PUBLICATIONS

International Preliminary Report on Patentability received for PCT Patent Application No. PCT/US2020/052157, mailed on Apr. 7, 2022, 10 pages.

(Continued)

*Primary Examiner* — Jill A Warden
*Assistant Examiner* — Michael Stanley Gzybowski
(74) *Attorney, Agent, or Firm* — Workman Nydegger (57) ABSTRACT

A biological sample collection system can include a sample collection vessel having a closed first end and an open second for receiving a biological sample. The system can additionally include a sealing cap configured to associate with the sample collection vessel, a reagent chamber secured within an interior space of the sealing cap and retaining a measure of sample preservation solution, a shim circumferentially associated with a proximal end of the reagent chamber and spanning the distance between the reagent chamber and the interior sidewall of the sealing cap, and a plug having a diaphragm configured to selectively engage the shim and form a seal for retaining the sample preservation solution within the reagent chamber. Associating the sealing cap with the sample collection vessel displaces the diaphragm from the shim and breaks the seal formed therebetween, opening a fluid path between the reagent chamber and the sample collection chamber.

19 Claims, 4 Drawing Sheets

(56) References Cited

U.S. PATENT DOCUMENTS

| | | |
|---|---|---|
| D357,985 S | 5/1995 | Burns |
| 5,422,273 A | 6/1995 | Garrison et al. |
| 5,924,584 A | 7/1999 | Hellstrom et al. |
| D425,625 S | 5/2000 | Niermann |
| 6,171,287 B1 | 1/2001 | Lynn et al. |
| 6,402,413 B1 | 6/2002 | Schwartzman |
| 6,426,049 B1 | 7/2002 | Rosen et al. |
| 7,427,005 B1 | 9/2008 | Lohrman |
| D650,088 S | 12/2011 | Motadel |
| D667,960 S | 9/2012 | Wilkinson |
| D743,571 S | 11/2015 | Jackson et al. |
| D776,291 S | 1/2017 | Wan et al. |
| D852,375 S | 6/2019 | Druga et al. |
| D860,472 S | 9/2019 | Blake et al. |
| D924,430 S | 7/2021 | Johnson |
| D930,184 S | 9/2021 | Johnson |
| 11,284,867 B2 | 3/2022 | Johnson |
| 2005/0014273 A1 | 1/2005 | Dahm et al. |
| 2007/0134134 A1 | 6/2007 | Watts et al. |
| 2008/0251489 A1 | 10/2008 | Livingston et al. |
| 2009/0120214 A1 | 5/2009 | Gross |
| 2009/0162930 A1 | 6/2009 | Grimes et al. |
| 2009/0216213 A1 | 8/2009 | Muir et al. |
| 2009/0259145 A1 | 10/2009 | Bartfeld et al. |
| 2010/0210010 A1 | 8/2010 | Lee et al. |
| 2010/0252116 A1 | 10/2010 | Kilcoin et al. |
| 2011/0052459 A1 | 3/2011 | Shibata et al. |
| 2011/0263007 A1 | 10/2011 | Stordeur et al. |
| 2012/0193362 A1 | 8/2012 | Porter |
| 2014/0087413 A1 | 3/2014 | Newbold et al. |
| 2014/0312065 A1 | 10/2014 | Rohr et al. |
| 2016/0003861 A1 | 1/2016 | Brennan et al. |
| 2016/0145091 A1 | 5/2016 | Imai et al. |
| 2018/0036733 A1 | 2/2018 | Williams |
| 2018/0193831 A1 | 7/2018 | Hopper |
| 2018/0372595 A1 | 12/2018 | Pais et al. |
| 2019/0151842 A1 | 5/2019 | Williams et al. |
| 2020/0156056 A1 | 5/2020 | Williams et al. |

FOREIGN PATENT DOCUMENTS

| | | |
|---|---|---|
| CN | 207271282 U | 4/2018 |
| CN | 306013714 S | 8/2020 |
| FR | 1285993 A | 3/1962 |
| JP | 63-070954 U | 5/1988 |
| JP | 2011-513754 A | 4/2011 |
| WO | 2005/120977 A1 | 12/2005 |
| WO | 2017/019598 A1 | 2/2017 |
| WO | 2017/145102 A1 | 8/2017 |

OTHER PUBLICATIONS

International Search Report and Written Opinion received for PCT Patent Application No. PCT/US2020/052157, mailed on Feb. 10, 2021, 13 pages.

Invitation to Pay Additional Fees received for PCT Patent Application No. PCT/US20/052157, mailed on Dec. 8, 2020, 2 pages.

Our Team, Helping Your Team Get Back in the Game | Saliva Collection Systems for COVID-19 Testing. Online, published date Oct. 8, 2020. Retrieved on Jul. 15, 2022 from URL: https://www.youtube.com/watch?v=k5Vitp5dtqc.

European Search Report received for EP Patent Application No. 20868861.4, mailed on Sep. 1, 2023, 7 pages.

Li Yanbin et al., "Classification, Structure and Selection of Full Automatic Biochemical Analyser", China Medical Device Information, No. 3, Mar. 15, 2008.

SAMPLE COLLECTION KIT INCLUDING CAP HAVING SELECTIVELY OPENABLE DIAPHRAGM VALVE

CROSS-REFERENCE TO RELATED APPLICATIONS

This application claims priority to and the benefit of U.S. Provisional Patent Application Ser. No. 62/904,080, filed Sep. 23, 2019 and titled "SAMPLE COLLECTION KIT INCLUDING CAP HAVING SELECTIVELY OPENABLE DIAPHRAGM VALVE," which is incorporated herein by this reference in its entirety.

BACKGROUND

Technical Field

This disclosure generally relates to vials and vessels for collecting and storing biological samples. More specifically, the present disclosure relates to systems and kits for the collection and preservation of biological samples for future testing in a laboratory or other biological sample analysis facility.

Background and Relevant Art

Field collection of biological samples can provide scientists, physicians, geneticist, epidemiologists, or similar personnel with invaluable information. For example, access to a fresh sample of a patient's blood, purulent discharge, or sputum can help a physician or epidemiologist to isolate or identify a causative agent of infection. Similarly, a saliva sample can permit a scientist or geneticist access to the requisite nucleic acid for genetic sequencing, phylotyping, or other genetic-based studies. In the foregoing examples, in addition to many other situations, it is desirable to work with a fresh biological sample to ensure procurement of accurate results. However, isolation of the probative composition (e.g., nucleic acid, proteins, chemicals, etc.) often requires use of specialized equipment and often benefits from controlled laboratory conditions.

It can be inconvenient and sometimes improbable to require patients/individuals to travel to a biological sample collection center having the appropriate equipment and desirable controlled environment for sample preparation. Similarly, it may be difficult for personnel to directly access the patient/individual, particularly if the sample size is large and/or geographically diverse (e.g., as can be found in large genetic studies of thousands of individuals across an entire country, ethnic population, or geographic region). Further complicating this issue, it is often beneficial to immediately process any procured biological sample, and field personnel may be limited by lack of access to appropriate specialized equipment or to a controlled environment for high-fidelity sample processing.

Some biological sample collection devices and kits have addressed some of the foregoing issues. For example, some commercial kits provide a user with a vial for receiving a biological sample and a preservation reagent that can be added to the collected biological sample, acting to preserve elements within the biological sample (to a certain extent and for a period of time). However, implementations of self-collection systems often rely on inexperienced or untrained individuals to deposit the biological sample into the receiving vessel. This presents a number of problems, including, for example, technical training and precise measurements often required to properly preserve the biological sample for later processing. In the absence of such, it is important to provide a biological sample collection system that can be easily implemented by a novice user and which can preserve the received biological sample for later processing.

Accordingly, there are a number of disadvantages with biological sample collection and preservations systems that can be addressed.

BRIEF SUMMARY

Embodiments of the present disclosure solve one or more of the foregoing or other problems in the art with kits, apparatuses, and methods for collecting and preserving a biological sample. In particular, one or more embodiments can include a biological sample collection system having a sample collection vessel spanning between a closed first end and a second end defining an opening for receiving a biological sample into a sample collection chamber defined within the sample collection vessel. The biological sample collection system can additionally include a sealing cap configured to associate with the second end of the sample collection vessel, a reagent chamber configured to secure within an interior space defined by the sealing cap and to retain a measure of sample preservation solution therein, a shim configured to circumferentially associate with a proximal end of the reagent chamber and to span a distance between the proximal end of the reagent chamber and an interior sidewall of the sealing cap, and a plug having a diaphragm sized and shaped to fit within the opening of sample collection vessel and configured to selectively engage the shim and form a seal to retain the measure of sample preservation solution within the reagent chamber. Associating the sealing cap with the sample collection vessel displaces the diaphragm from the shim and breaks the seal formed therebetween, opening a fluid path between the reagent chamber and the sample collection chamber.

In one aspect, the sample collection vessel includes a connection member and the sealing cap includes a complementary connection member configured to associate with the connection member of the sample collection vessel and to couple the sample collection vessel and the sealing cap. In one aspect, the connection member is a ridge projecting away from the sample collection vessel or a depression within the sample collection vessel and the complementary connection member is a hook or ridge sized and shaped to engage the connection member. In one aspect, the connection member and the complementary connection member are interlocking threads.

In one aspect, the sample collection system is provided in the form of a separable two-piece sample collection system. Such a system can include (i) the sample collection vessel as a first piece of the separable two-piece sample collection system and (ii) a cap assembly as a second piece of the separable two-piece sample collection system. The cap assembly includes the sealing cap, the reagent chamber secured within the interior space of the sealing cap, the shim circumferentially associated with the proximal end of the reagent chamber and spanning the distance between the proximal end of the reagent chamber and the interior sidewall of the sealing cap, and the plug engaging the shim and sealing the measure of sample preservation solution within the reagent chamber.

In one aspect, the plug includes a plug body configured to insert within an interior portion of the proximal end of the reagent chamber. The reagent chamber can include a connection element configured to abut the plug body and to break the seal between the diaphragm and the shim. In one aspect, the interior portion of the proximal end of the reagent chamber has one or more protrusions extending therefrom that are configured to engage the plug body and form a space between an outer sidewall of the plug body and an interior sidewall of the proximal end of the reagent chamber. In one aspect, the space is a portion of the fluid path that permits the measure of sample preservation solution to pass around the outer sidewall of the plug body, and when the seal is broken between the diaphragm and the shim, around the diaphragm.

In one aspect, the diaphragm of the plug is an annular diaphragm spatially offset from a bottom opening of the reagent chamber and engaging the shim. In such an aspect, the fluid path between the reagent chamber and the sample collection chamber is obstructed by the shim and the annular diaphragm when the plug is engaged with the shim, and the fluid path is unobstructed when the plug is disengaged from the shim by associating the sealing cap with the sample collection vessel.

In one aspect, the reagent chamber includes a retaining ring configured to secure the reagent chamber with a reagent chamber connection member disposed within the interior space of the sealing cap. In one aspect, the reagent chamber connection member can include a sidewall protrusion sized and shaped to retain the reagent chamber in association with the sealing cap.

In one aspect, the shim includes a guide member sized and shaped to be received by a guide channel of the sealing cap.

In one aspect, the shim includes a sealing protrusion configured to form a fluid-tight connection between the shim and the proximal end of the reagent chamber and additionally includes a sample collection chamber sealing surface that forms a fluid-tight seal between the shim and the opening of the sample collection chamber when the sealing cap is associated with the sample collection vessel.

In one or more embodiments, a biological sample collection system can include a sample collection vessel having a sample collection chamber with an opening to receive a biological sample into the sample collection chamber and a ring structure formed on an interior sidewall of the sample collection vessel. The biological sample collection system additionally includes a sealing cap having a reagent chamber with sample preservation solution stored therein. The sealing cap is configured to associate with the sample collection vessel and cause the sample preservation solution to be dispensed from the reagent chamber and into the sample collection chamber. The biological sample collection system additionally includes a selectively openable diaphragm valve associated with the sealing cap and configured to transition from a closed configuration to an open configuration upon association of the sealing cap with the sample collection vessel. The selectively openable diaphragm valve includes a plug associated with a proximal end of the reagent chamber and having an annular diaphragm that is spatially offset from an opening of the proximal end of the reagent chamber. The selectively openable diaphragm valve also includes an annular shim surrounding and in fluid-tight communication with the reagent chamber. A bottom opening defined by the annular shim engages the annular diaphragm in the closed configuration to form a fluid-tight seal therebetween. The fluid-tight seal formed between the annular shim and the annular diaphragm obstructs a fluid path of sample preservation solution when in the closed configuration, and associating the sealing cap with the sample collection vessel causes the selectively openable diaphragm valve to transition to the open configuration by moving the reagent chamber and the plug relative to the annular shim and thereby breaking the fluid-tight seal between the annular shim and the annular diaphragm, opening the fluid path, and permitting the sample preservation solution to be dispensed from the reagent chamber and into the sample collection chamber.

In one aspect, the annular shim has a larger outer diameter than an inner diameter of the interior sidewall of the sample collection vessel formed by the ring structure.

In one aspect, the ring structure is configured to temporarily retain the annular shim in a fixed position relative to the sample collection vessel, and the plug is operable to move relative to the annular shim to unseal and/or reseal with the shim.

The present disclosure also includes kits for collecting and preserving biological samples. In some embodiments, a kit for collecting and preserving a biological sample includes (i) a sample collection vessel spanning between a closed first end and a second end having an opening to receive a biological sample into a sample collection chamber defined within the sample collection vessel, (ii) a funnel configured to selectively engage the second end of the sample collection vessel and guide receipt of a biological sample from a user into the sample collection chamber of the sample collection vessel, and (iii) a sealing cap assembly configured to selectively engage the second end of the sample collection vessel. The sealing cap assembly includes a sealing cap having a connection member configured to couple the sealing cap to the sample collection vessel and form a fluid-tight connection therebetween, a reagent chamber secured within an interior space defined by the sealing cap, a shim circumferentially associated with a proximal end of the reagent chamber and spanning a distance between the proximal end of the reagent chamber and an interior sidewall of the sealing cap to form a fluid-tight seal therebetween, and a plug having a plug body and a diaphragm associated with the plug body. The diaphragm of the plug is sized and shaped to fit within the opening of sample collection vessel and to form a seal with the shim to retain a measure of sample preservation solution within the reagent chamber.

In one aspect, the sealing cap assembly of the kit is configured to transition from a closed configuration to an open configuration upon coupling of the sealing cap with the sample collection vessel such that the plug and the shim are displaced in the open configuration, breaking the seal and allowing the measure of sample preservation solution to flow around the plug and into the sample collection chamber.

Accordingly, systems, methods, and kits for collecting a biological sample are disclosed herein. This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Embodiments of the present disclosure address one or more problems in the art of systems, kits, and/or methods for collecting and preserving a biological sample. A biological sample can be collected and its contents evaluated for various reasons, including, for example, identifying or characterizing a causative agent of disease (e.g., for treatment of the affected individual, for epidemiological reasons, etc.) or for genetic analysis of a subject's nucleic acid (e.g., genetic phylotyping, gene expression studies, genome sequencing, etc.). In most instances, including within the foregoing examples, it is desirous that the fidelity of the biological sample is maintained so that it retains its probative value.

However, collecting and preparing biological samples for analysis has traditionally been an endeavor for the skilled technician or specialized professional. This is problematic for obvious reasons, including the time and cost associated with individually collecting and transporting biological samples, particularly when the subjects reside in disparate rural locations and require service from personnel with the proper skill set to properly collect and preserve the biological sample.

Embodiments of the present disclosure provide sample collection and preservation systems and kits, and methods for using the same, which address one or more of the foregoing problems. For example, utilizing systems, kits, and methods for collecting and preserving biological samples, as disclosed herein, remove the need of specialized personnel when collecting and initially preserving a biological sample. Furthermore, sample collection and preservation are simplified, which decreases the likelihood that even an unskilled user will err when collecting and preserving a biological sample. As an illustrative example of the foregoing, biological sample collection kits disclosed herein include at least a two-piece sample collection and preservation system. A first portion includes a sample collection vial or vessel, which can be detachably associated with a funnel. When used, the funnel acts to guide the receipt of a biological sample from a user into the sample collection chamber of the collection vial or vessel. The funnel can also make it easier for a user to engage the collection vial and deposit a biological sample into the sample collection chamber. After depositing the requisite amount of biological sample, a user can remove the funnel (if used) and associate the second portion of the two-piece sample preservation system—e.g., a sealing cap associated with a reagent chamber—with the collection vial. The reagent chamber has been pre-filled with a predetermined amount of sample preservation reagent(s), and as the sealing cap is drawn down to seal the received biological sample within the sample collection chamber, the reagent(s) are released from the reagent chamber and into the sample collection chamber, mixing with and preserving the received biological sample.

As described in more detail below, the reagent chamber may fit within the sealing cap and can be fluid-tight on all sides except for one or more openings on a bottom thereof. This allows, in some instances, for the sample preservation fluid to be initially disposed only in the reagent chamber, such that the sealing cap holds no sample preservation reagent. Advantageously, this eliminates the need for a fluid-tight seal between the reagent chamber and the sealing cap (e.g., in other systems, the sealing cap holds the fluid and an intermediate retention chamber abuts the sealing cap, necessitating a fluid-tight seal between the intermediate retention chamber and the sealing cap).

Furthermore, the bottom of the reagent chamber may be configured for receiving a plug element. An annular diaphragm of the plug element may be offset from the opening(s) of the bottom of the reagent chamber so as not to obstruct the opening(s). Additionally, when the sample collection system is in a closed configuration, a shim is positioned around both the reagent chamber and the plug element, forming a fluid-tight seal at the interface between the shim and the annular diaphragm of the plug and between the shim and the reagent chamber. In such configuration, reagent within the reagent chamber does not enter the plug element, or stated another way, the plug element does not form a reservoir for the reagent. Instead, the plug defines a portion of the boundary of a closed reagent chamber. The interior wall of the shim can include a sealing ring extending inwardly therefrom which interfaces with an exterior wall of the reagent chamber and forms a fluid-tight seal therebetween. Advantageously, this structure allows the fluid-tight seal to persist even when the reagent chamber is advanced through the shim (e.g., to open a fluid path between the reagent chamber and the sample collection chamber, as described hereinbelow) and eliminates the need for tapering the reagent chamber and/or the shim to form a fluid-tight seal.

Further advantageously, the annular diaphragm of the plug is configured for forming a fluid-tight engagement with the interior sidewall of the shim. The fluid path between the reagent chamber and the sample collection chamber is opened, in some instances, by advancing the reagent chamber and plug through the shim such that the annular diaphragm of the plug disengages from the interior sidewall of the shim (extending fully through the shim and into the sample collection chamber). In some embodiments, the reagent chamber and plug are advanced through the shim by associating the sealing cap with the sample collection chamber (e.g., by threading the sealing cap over the sample collection vessel). Reagent(s) previously stored in the reagent chamber can thereby be released into the sample collection chamber through the fluid path(s). In this open configuration, the plug extends into the sample collection chamber and can additionally act as an agitator of fluid and sample when shaken.

In some embodiments, the opening of the selectively openable diaphragm valve is reversible. For example, disassociating the sealing cap from the sample collection vessel can cause the selectively openable diaphragm valve to close by causing the annular diaphragm of the plug to retract into the shim to re-engage in fluid-tight manner therewith (while the fluid-tight connection between the shim and the reagent chamber persists by virtue of the sealing ring of the shim).

As can be appreciated from the foregoing, in addition to alternative and/or additional embodiments provided herein, the systems, kits, and methods of the present disclosure can be used by skilled or unskilled individuals with reduced likelihood of error associated with collecting and at least initially preserving a biological sample. Accordingly, implementations of the present disclosure can reduce the cost associated with procuring biological samples for diagnostic, scientific, or other purposes and can increase the geographic reach of potential sample collection areas without the need of establishing the necessary infrastructure (e.g., controlled environments conducive to sample collection and preservation, skilled personnel to physically collect, transport, and/or preserve the biological samples, etc.).

As used herein, the term "biological sample" can include any cell, tissue, or secretory fluid (whether host or pathogen related) that can be used for diagnostic, prognostic, genetic, or other scientific analysis. This can include, for example, a human cell sample such as skin. It can also include a non-human cell sample that includes any of a bacterium, virus, protozoa, fungus, parasite, and/or other prokaryotic or eukaryotic symbiont, pathogen, or environmental organism. The term "biological sample" is also understood to include fluid samples such as blood, urine, saliva, and cerebrospinal fluid and extends to other biological samples including, for example, mucus from the nasopharyngeal region and the lower respiratory tract (i.e., sputum).

As used herein, the "probative component" of the biological sample refers generally to any protein, nucleic acid, surface moiety, or other compound that can be isolated from the biological sample. Preferably, the probative component is or includes nucleic acid, more preferably DNA. In a preferred embodiment, the biological sample is or includes saliva, which presumptively contains a preferable probative component in the form of the user's genetic material (e.g., DNA and RNA).

Multi-Part Self-Contained Sample Collection System/Kit

In one embodiment, a biological sample is collected, preserved, and stored in a collection vessel as part of a multi-piece, self-contained sample collection system or kit. A first piece of the system or kit includes a collection vessel, a second piece includes a sample collection funnel, which may be packaged separately from or removably connected to the collection vessel, and a third piece includes a sealing cap having a selectively openable diaphragm valve comprised of a plug and a shim and a reagent chamber disposed within or integrated with the sealing cap. The sealing cap is configured to associate with the collection vessel, to dispense sample preservation reagents into the collection vessel through the selectively openable diaphragm valve, and to seal the contents therein.

Figure 1:
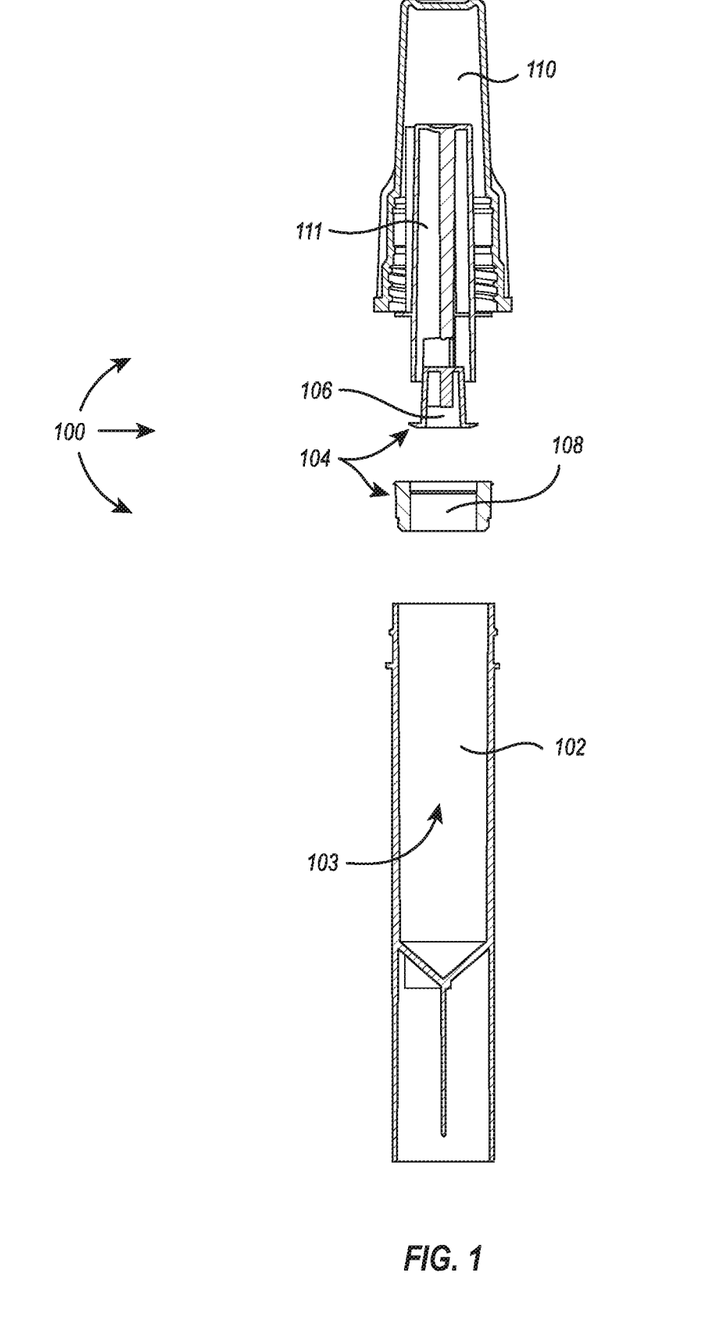
FIG. 1 illustrates an exploded, cross-sectional view of a three-dimensional model of an exemplary sample collection system that includes a cap configured to receive a selectively openable diaphragm valve, in accordance with one or more embodiments of the present disclosure.

For example, FIG. 1 illustrates an exploded view depicting a biological sample collection system or kit 100. The system 100 includes a collection vessel 102 and, optionally, a funnel (not shown), which can be associated with a top portion of the collection vessel 102 and placed in fluid communication with a sample collection chamber 103 of the collection vessel 102. The biological sample collection system 100 can also include a selectively openable diaphragm valve 104 comprised of a plug 106 and a shim 108 associated with a sealing cap 110 that has a reagent chamber 111 disposed within or integrated with the sealing cap 110. The sealing cap 110—together with the selectively openable diaphragm valve 104—can be sized and shaped to associate with a top portion of the collection vessel 102, fitting over and sealing an opening of the sample collection chamber 103.

In some embodiments, the reagent(s) within the reagent chamber 111 include a preservation or buffering solution that protect the integrity of the probative component of the biological sample prior to purification or testing. Preservation reagents are typically chemical solutions and may contain one or more salts (e.g., NaCl, KCl, $Na_2HPO_4$, $KH_2PO_4$, or similar, and which may, in some implementations, be combined as a phosphate buffered saline solution, as known in the art), lysing agents (e.g., detergents such as Triton X-100 or similar), chelating agents (e.g., ethylenediaminetetraacetic acid (EDTA)), ethylene glycol-bis(β-aminoethyl ether)-N,N,N',N'-tetraacetic acid (EGTA), or similar), distilled water, or other reagents known in the art. In one or more embodiments, the reagent or buffering solution stabilizes at least one probative component within the sample (e.g., nucleic acids, such as DNA and RNA, protein, etc., and combinations thereof) during transfer, transportation, and/or storage at a laboratory, clinic, or other destination. In some embodiments, the sample can be stored, at or below room temperature after the preservation solution is added, for weeks or months without significant loss of the probative component. That is, the sample can still be utilized for diagnostic, genetic, epidemiologic, or other purposes for which it was collected after storage for weeks or months in the preservation solution.

Figure 2:
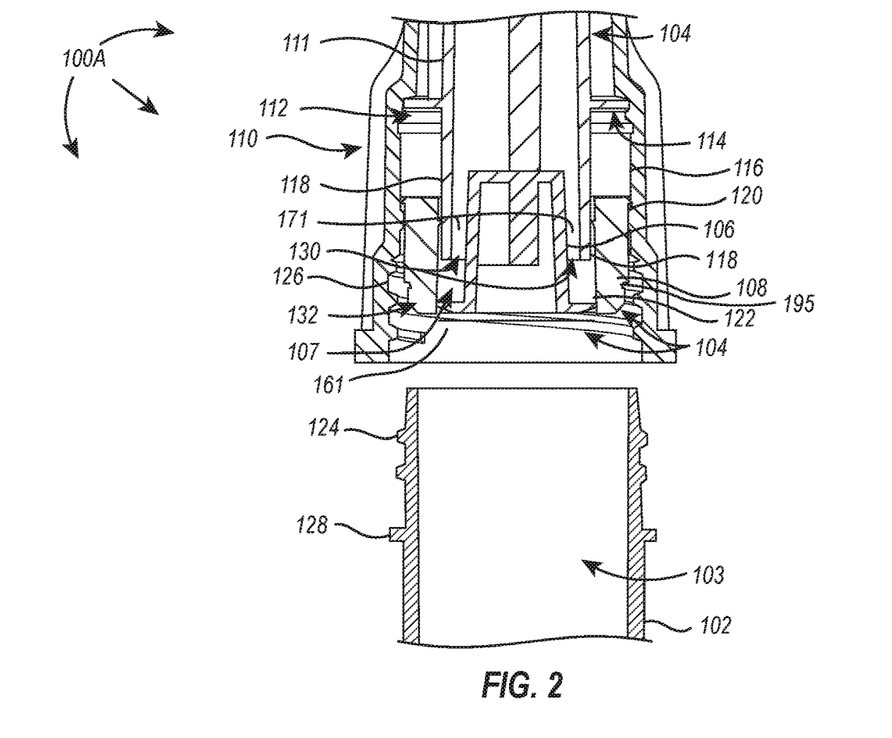
FIG. 2 illustrates a cross-sectional view of a portion of a cap from a sample collection system that is configured with a selectively openable diaphragm valve in a closed position, the cap being depicted as aligned with but not engaging the opening of a complementary sample collection vessel, in accordance with one or more embodiments of the present disclosure.

With continued reference to FIG. 1, the sealing cap 110 and a saliva funnel (not shown) can each independently attach to the sample collection vessel 102 using a connection mechanism. The connection mechanism can include, for example, threads, snap or press fit connections, tongue and groove members, bayonet connection, or other interlocking or mechanically coupling mechanisms. For example, a funnel can be first attached to the sample collection vessel 102 via complementary connection mechanisms (e.g., complementary threads; not shown). After facilitating receipt of a biological sample from a user, the funnel can be removed by reversing the complementary connection mechanism (e.g., unscrewing the funnel; not shown), and a sealing cap 110 can be secured to the collection vessel 102 using a same or similar complementary connection mechanism, as shown in FIG. 2. That is, the sealing cap 110 can include connection members 126 (e.g., threads) located on an inner circumferential wall of the sealing cap 110 that are complementary to and work in conjunction with the connection members 124 (e.g., complementary threads) disposed on an exterior surface of the sample collection vessel 102.

Figure 3:
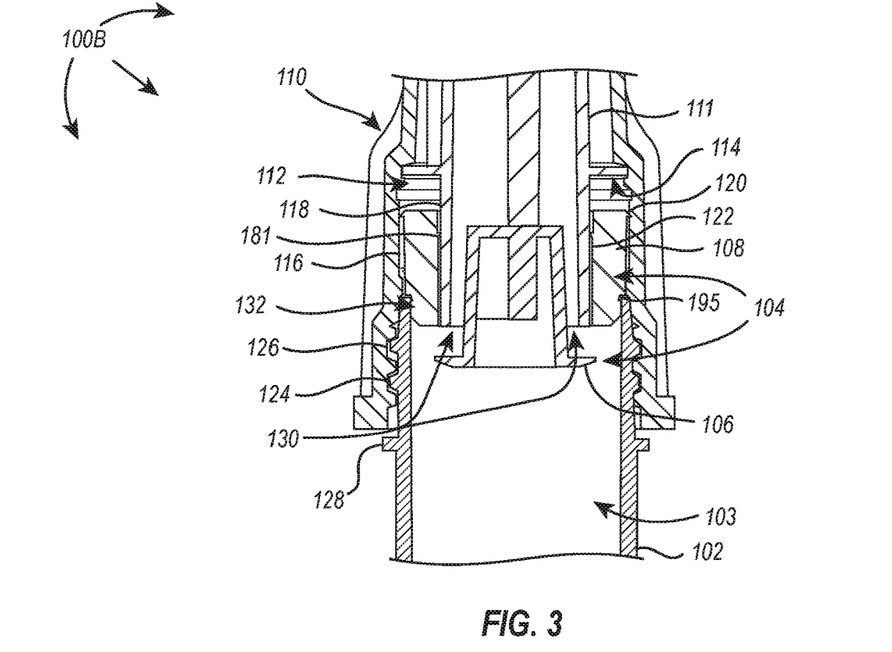
FIG. 3 illustrates the cross-sectional view of FIG. 2 with the cap being depicted as secured to the sample collection vessel and the selectively openable diaphragm valve depicted in an open position, in accordance with one or more embodiments of the present disclosure.
Figure 10:
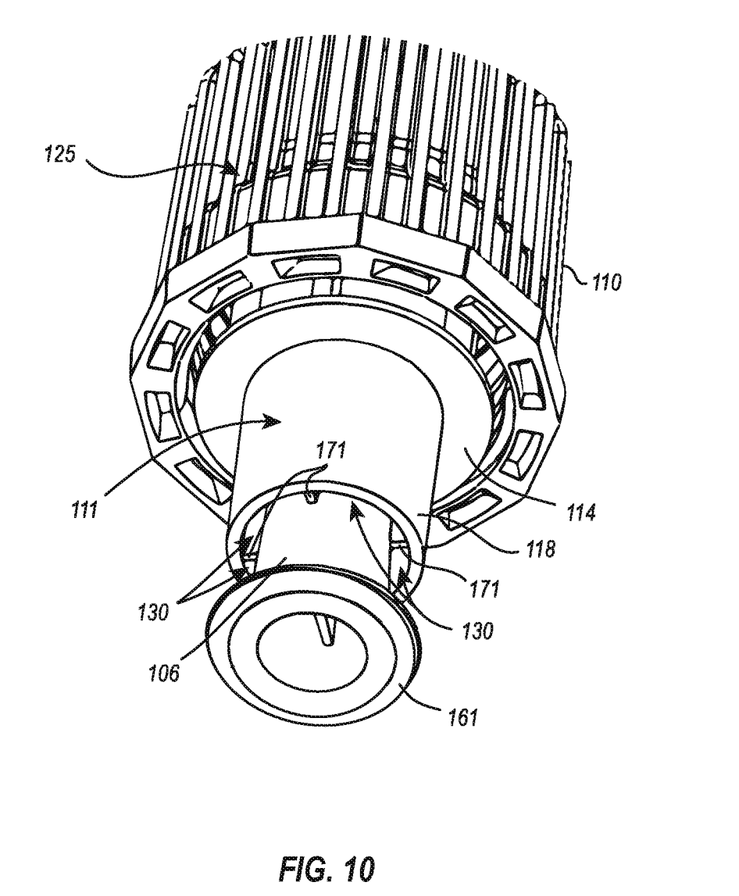
FIG. 10 illustrates a bottom perspective view of a selectively openable diaphragm valve in an open configuration.

In some embodiments, the connection mechanism between the funnel and collection vessel is different than the connection mechanism between the solution cap and the collection vial. For example, the funnel may be press fit or snap fit onto the collection vessel, whereas the solution cap is rotationally secured through engagement of complementary threads located on an exterior portion of the collection vessel and an interior portion of the solution cap or vice versa. Regardless of the attachment mechanism used, a sample preservation fluid can be introduced into the sample collection chamber 103 of the sample collection vessel 102 and mixed with the deposited biological sample as a result of the sealing cap 110 being attached to the sample collection vessel 102. As provided earlier, this can be due to the selectively openable diaphragm valve 104 opening and allowing reagent(s) to be released through fluid vents 130 defined by the reagent chamber 111 and the plug 106 (as shown in FIGS. 3 and 10) and into the sample collection chamber 103.

In an embodiment, the sealing cap 110 receives a measure of reagents into the reagent chamber 111, and as shown by the cross-sectional views of the assembled biological sample collection system 100A in FIG. 2, a selectively openable diaphragm valve 104 (in a closed configuration) is associated with the sealing cap 110, sealing the reagents within the sealing cap 110. The reagent chamber 111 is snap-fittingly received into the sealing cap 110, in some instances creating a fluid tight connection. As illustrated, the reagent chamber 111 includes a retaining ring 114 which fits into a space formed by a protrusion 112 of the interior sidewall of the sealing cap 110, allowing the sealing cap 110 to stabilize the reagent chamber 111. In some embodiments, an upper collar 109 of the reagent chamber 111 extends into the sealing cap 110 and associates therewith via an interference fit.

As is shown in FIG. 2, the reagent chamber includes one or more connection elements 171. As shown, the connection elements receive and hold secure the plug 106 such that the plug becomes coupled with the reagent chamber 111 (e.g., via a friction fit). The connection elements 171 of FIG. 2 (see also FIG. 4) are protrusions extending inward from an interior sidewall of the reagent chamber 111. For instance, when the plug 106 is coupled to the reagent chamber 111, spaces exist between the inward protrusion connection elements 171, an exterior sidewall of the plug, and an interior sidewall of the reagent chamber 111, thereby forming fluid vents 130. In some instances, the plug 106 includes one or more corresponding connection elements (not shown) for coupling the plug to the reagent chamber 111.

As further illustrated by FIG. 2, the selectively openable diaphragm valve 104 includes a reagent retention chamber 107 in fluid communication with the reagent chamber 111 via fluid vents 130. The reagent retention chamber is formed by the plug 106 and the shim 108, with an annular diaphragm 161 of the plug being in fluid-tight engagement with an interior sidewall 122 of the shim 108. The reagent chamber 111 defines fluid vents 130, through which reagent may be transferred from the reagent chamber 111 to the sample collection chamber 103. However, in FIG. 2, any reagent within the reagent chamber 111 would be retained, owing to the closed configuration of the selectively openable diaphragm valve 104. That is, as illustrated in FIG. 2, the fluid vents 130 open into the reagent retention chamber 107 formed by the annular diaphragm 161 of the plug 106 being in fluid-tight engagement with the interior sidewall 122 of the shim 108. When in a closed configuration, as shown in FIG. 2, the reagent retention chamber 107 obstructs the fluid path between the reagent chamber 111 and the sample collection chamber 103.

An interior sidewall 122 of the shim 108 defines an aperture into which the reagent chamber 111 extends, and the interaction between the interior sidewall 122 of the shim 108 and the exterior sidewall 118 of the reagent chamber 111 creates a fluid tight connection. For example, as shown in FIGS. 2 and 3, the interior sidewall 122 of the shim 108 includes a sealing ring 181 (e.g., composed of an elastic material). The sealing ring 181 extends inward from the interior sidewall 122 of the shim 108 and interacts with the exterior sidewall 118 of the reagent chamber 111 to form a fluid-tight seal between the interior sidewall 122 and the exterior sidewall 118. The fluid-tight seal persists even when the position of the reagent chamber 111 is changed with respect to the shim 108. The fluid tight connection between the shim 108 and the reagent chamber 111 also prevents the reagents within the reagent retention chamber 107 from passing into the sample collection chamber 103.

It will be appreciated that other structures for forming a fluid-tight seal between the shim and the reagent chamber are within the scope of this disclosure. For example, the interior sidewall 122 of the shim 108 and the exterior sidewall 118 of the reagent chamber 111 may be tapered in a complementary manner, such that a fluid-tight seal is maintained along the interface between the reagent chamber 111 and the shim 108 even when the sealing cap 110 becomes associated with the sample collection vessel 102.

As also shown in FIG. 2, the shim 108 associates with sealing cap 110. A guide member 120 of the shim 108 protrudes away from the body of the shim 108 and extends into a guide channel 116 formed by the interior surface of the sealing cap 110. The guide member 120 acts, in some embodiments, to retain the shim 108 in association with the sealing cap 110.

Furthermore, as shown in FIG. 3 (and in FIG. 2, where the selectively openable diaphragm valve 104 is in a closed configuration), the shim 108 associates with the opening of the sample collection chamber 103. The shim 108 additionally includes a lower collar 132 that associates with the interior sidewall of the sample collection chamber 103. In some embodiments, the lower collar 132 associates with the sample collection chamber 103 via an interference fit, which can serve to stabilize the selectively openable diaphragm valve 104, the sealing cap 110, and the sample collection vessel 102. In some embodiments, the interference fit between the shim 108 and the sample collection chamber 103 is a liquid-tight fit.

As the complementary threads 124, 126 between the sealing cap 110 and the sample collection vessel 102 are inter-engaged and the sealing cap 110 is advanced towards the sample collection vessel 102, the plug 106—which is coupled to the reagent chamber 111—and the reagent chamber 111—which is coupled to the sealing cap 110—are similarly advanced. As shown in FIG. 3, the reagent chamber 111 and the plug 106 are pushed through the aperture defined by the shim 108, positioning the selectively openable diaphragm valve 104 in an open configuration. In the open configuration depicted in FIG. 3, the annular diaphragm 161 of the plug 106 is disengaged from the interior sidewall of the shim 108, thereby opening the reagent retention chamber 107 (shown in FIG. 2) to open a fluid path between the reagent chamber 111 and the sample collection chamber 103. Reagent(s) within the reagent chamber 111 can now freely pass through the fluid vents 130, through the now-open selectively openable diaphragm valve 104, and into the sample collection chamber 103.

In the embodiment shown in FIG. 3, as the sealing cap 110 is associated with the sample collection vessel 102 after the lower collar 132 of the shim 108 is associated with the interior sidewall of the sample collection chamber 103, the shim 108 does not move relative to the sample collection vessel 102. The sealing cap 110, the reagent chamber 111, and the plug 106 advance relative to the shim 108 and the sample collection vessel 102. In some embodiments, the body of the shim 108 above the lower collar 132 has a larger diameter than the lower collar 132, and this larger diameter body does not fit within the opening of the sample collection chamber 103. Instead, it abuts and is impeded by the upper rim of the sample collection chamber 103 that defines the opening thereof. This prevents the shim 108 from advancing along with the reagent chamber 111 and the solution cap 110 toward sample collection vessel 102. The resistive force impeding progress of the shim 108 is greater than the frictional force between the plug 106 and the shim 108, and the torque (or other force) applied to the solution cap 110 to associate the solution cap 110 with the sample collection vessel 102 is greater than the frictional force between the plug 106 and the shim 108. Accordingly, the selectively openable diaphragm valve 104 undergoes a conformational change where the plug 106 advances through the shim 108, revealing the fluid vents 130 (as shown in FIG. 3).

As shown in FIGS. 2 and 3, the guide member 120 moves along the guide channel 116 as the solution cap 110 threadedly secures to the sample collection vessel 102.

In some embodiments, the distance required to open the selectively openable diaphragm valve 104 is proportional to the distance required to advance the annular diaphragm 161 of the plug 106 beyond the shim 108 and into the sample collection chamber 103 (after the shim is in contact with the upper rim of the sample collection chamber 103). This distance may be the same or less than the distance between the terminal edge of the solution cap 110 and a stop member 128 disposed on the external surface of the sample collection vessel 102 when the connection members 124, 126 thereof initially engage.

Although, as shown, four fluid vents 130 are formed when the plug 106 is coupled to the reagent chamber 111 (e.g., see FIG. 10, whereby the four fluid vents 130 are formed when the plug 106 is abutting the four inwardly protruding connection elements 171 of the reagent chamber 111), it should be appreciated that in some embodiments there can be more or fewer fluid vents. For example, additional or fewer fluid vents may be formed by increasing or decreasing the number of connection elements 171 of the reagent chamber 111. In some embodiments, the connection elements 171 separating the fluid vents 130 can be a different shape (e.g., a single inwardly protruding elongated arcuate element) and/or the selectively openable diaphragm valve 104 may operate differently than illustrated in FIGS. 2 and 3. For example, rather than inwardly protruding elements 171, the reagent chamber 111 may include a connection element comprising threads, with the plug 106 including corresponding threads on a top portion thereof (e.g., the portion opposite the annular diaphragm 161) such that a single annular fluid vent 130 is formed when the plug 106 is coupled to the reagent chamber 111.

With continued reference to FIGS. 2 and 3, in some embodiments, the selectively openable diaphragm valve is selectively and reversibly unsealed and resealed (e.g., selectively openable and closable). In some instances, the lower collar 132 of the shim 108 is formed of an elastic material and is of a diameter such that, when the lower collar 132 has associated with the upper rim of the sample collection chamber 103, the frictional force between the lower collar 132 and the sample collection chamber 103 is greater than a force necessary to cause the exterior sidewall 118 of the reagent chamber 111 to retract along the sealing ring 181 of the shim 108 (e.g., the force exerted when disassociating, as by unthreading, the sealing cap 110 from the sample collection vessel 102). As such, the shim 108 remains in a static position with respect to the sample collection vessel 102 when the sealing cap 110 becomes dissociated from the sample collection vessel 102 and the reagent chamber 111 and the plug 106 retract from the sample collection chamber 103. In some instances, the annular diaphragm 161 of the plug 106 re-engages with the interior sidewall 122 of the shim 108 while the lower collar 132 of the shim 108 remains in communication with the upper ridge of the sample collection chamber 103.

Subsequently, in some embodiments, the combined frictional force between the annular diaphragm 161 and the interior sidewall 122 and the frictional force between the exterior sidewall 118 of the reagent chamber and the sealing ring 181 is greater than a force necessary to disassociate the lower collar 132 from the upper rim of the sample collection chamber 103. Accordingly, after the plug 106 re-engages with the shim, the selectively openable diaphragm valve 104 becomes re-sealed, or closed, such that the fluid path between the fluid vents 130 and the sample collection chamber is obstructed. Continued dissociation of the sealing cap 110 from the sample collection vessel 102 (e.g., by unthreading) then causes the shim 108 to retract out of the sample collection vessel along with the plug 106 and the reagent chamber 111.

In other embodiments, to effectuate the re-sealing or selective closing functionality of the a selectively openable diaphragm valve 104, a detent 195 is formed within the lower collar 132 of the shim 108. The detent 195 can mechanically engage with a protruding retention ring on an interior sidewall of the sample collection chamber (not shown) when the shim 108 associates with the upper rim of the sample collection chamber. The ring-detent engagement can prevent the shim 108 from being pushed farther into the sample collection vessel, and can hold the shim 108 in place with respect to the sample collection chamber 103 when the sealing cap 110 is being disassociated from the sample collection vessel (e.g., by unthreading). The retention ring is configured, in some embodiments, to disengage from the detent 195 after the annular diaphragm 161 of the plug 106 has re-engaged with the interior sidewall of the shim 108 (thereby providing greater upward force on the shim 108 as the unthreading continues thereafter), such that the shim 108 may thereafter retract from the sample collection chamber along with the plug 106 and the reagent chamber 111.

Those skilled in the art will recognize, however, that embodiments of a selectively openable diaphragm valve that are not selectively closable are also within the scope of this disclosure.

Figure 4:
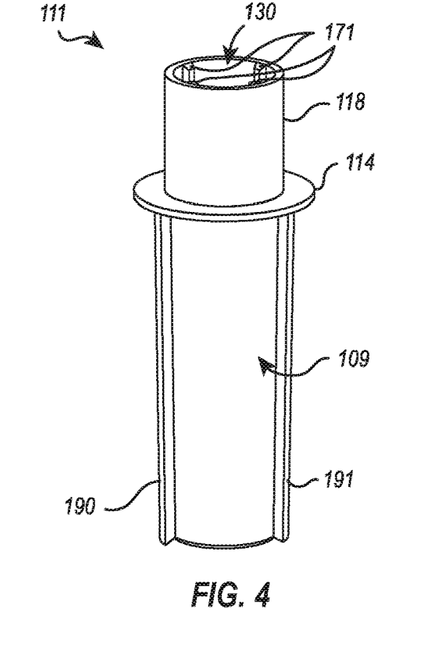
FIG. 4 illustrates a perspective view of the reagent chamber component of the exemplary selectively openable diaphragm valve of FIGS. 2 and 3, shown in isolation from other components of the corresponding selectively openable diaphragm valve, in accordance with one or more embodiments of the present disclosure.
Figure 5:
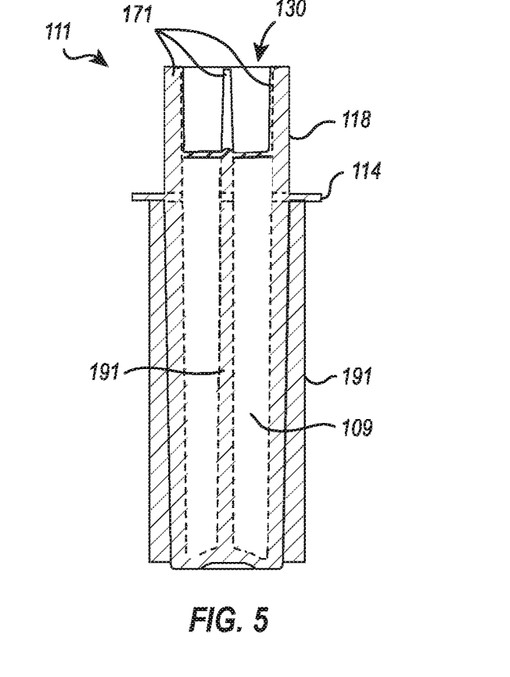
FIG. 5 illustrates a cross-sectional view of the reagent chamber of FIG. 4.

FIG. 4 illustrates a perspective view of an exemplary reagent chamber 111 of a sample collection system, and FIG. 5 illustrates a cross-sectional view of the same. As shown, the reagent chamber 111 includes one or more external protrusions 191 for stabilizing the reagent chamber 111 within the sealing cap 110. The body of the plug (not shown) is sized and shaped to fit within the proximal end of the reagent chamber, and as perhaps better shown in FIG. 5, the body of the plug may abut a platform formed within the interior space of the reagent chamber 111. The platform or connecting element can act to force the plug away from the shim when sealing the cap to the sample collection vessel (and thereby moving the diaphragm valve from a closed position to an open position). As shown, the connecting elements 171 protrude into the interior space of the proximal end of the reagent chamber (e.g., such that the plug body can be received in the space formed between the connecting elements 171). At a distance within the proximal end of the reagent chamber, the connecting elements 171 can protrude farther into the interior space such that they touch and form a crosswise platform (as shown) or otherwise prevent the plug body from entering farther into the interior space of the reagent chamber. In embodiments where the protruding connecting elements connect to form a crosswise platform, the reagent reservoir may be divided into compartments below the platform (i.e., separated by connecting elements). It should be appreciated that the volume of the reagent chamber can be adjusted based on the number and/or width of the protruding connecting elements and where (or whether) the protruding connecting elements connect.

Figure 6:
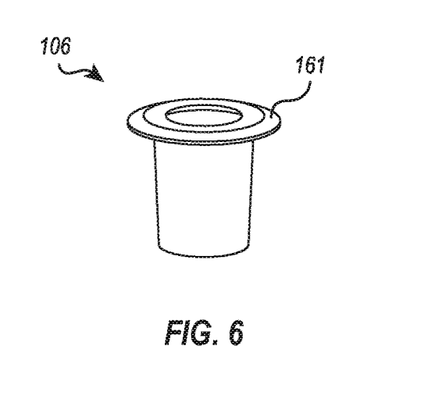
FIG. 6 illustrates a perspective view of a plug component of the exemplary selectively openable diaphragm valve of FIGS. 2 and 3, shown in isolation from other components of the corresponding selectively openable diaphragm valve, in accordance with one or more embodiments of the present disclosure.
Figure 7:
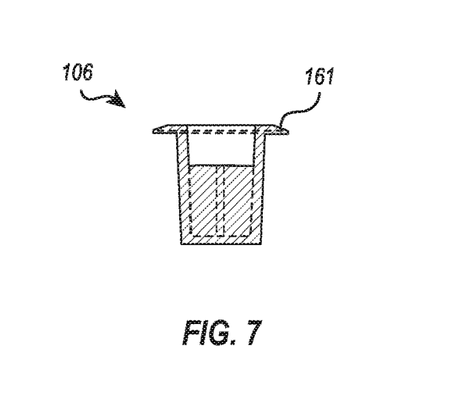
FIG. 7 illustrates a cross-sectional view of the plug of FIG. 6.

FIG. 6 illustrates a perspective view of an exemplary plug 106 of a selectively openable diaphragm valve 104 of a sample collection system, and FIG. 7 illustrates a cross-sectional view of the same. As previously described, the plug includes an annular diaphragm 161 configured to selectively engage with an interior sidewall of the shim 108. It should be appreciated that in some embodiments, such as that shown in FIGS. 6 and 7, the plug does not act as a reagent reservoir. That is, the surface of the plug facing the reagent reservoir is solid and does not retain sample preservation solution (or other reagent stored in the reagent reservoir) during use.

Figure 8:
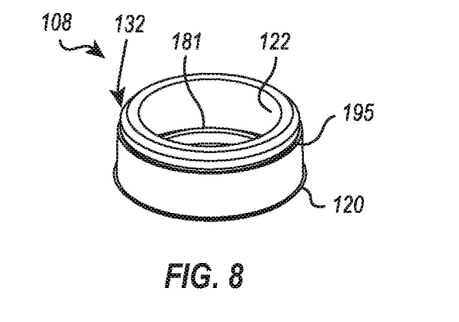
FIG. 8 illustrates a perspective view of the shim component of the exemplary selectively openable diaphragm valve of FIGS. 2 and 3, shown in isolation from other components of the corresponding selectively openable diaphragm valve, in accordance with one or more embodiments of the present disclosure.
Figure 9:
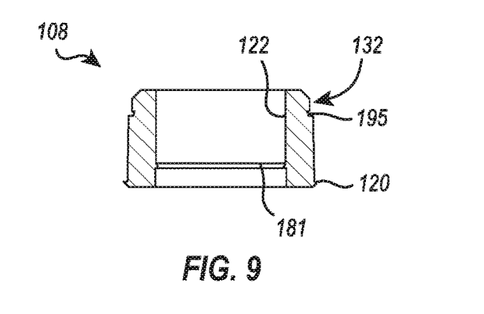
FIG. 9 illustrates a cross-sectional view of the shim of FIG. 8.

FIG. 8 illustrates a perspective view of a shim 108 of a selectively openable diaphragm valve 104 of a sample collection system, and FIG. 9 illustrates a cross-sectional view of the same. As shown, the shim 108 includes a guide member 120 that is configured for extending into a guide channel 116 of a sealing cap 110. The shim 108 also has a lower collar 132 for engagement with a top portion of a sample collection vessel 102. The shim 108 also has a sealing ring for forming a fluid-tight connection between the shim 108 and the reagent chamber 111. The interior sidewall 122 is additionally configured for selective engagement with a plug 106 (in particular, an annular diaphragm 161 of a plug).

FIG. 10 illustrates a perspective view of a plug of a selectively openable diaphragm valve coupled to a reagent chamber of a sample collection system. The sealing cap 110 may additionally include a plurality of external ridges 125. The external ridges 125 can facilitate a user to better grip the sealing cap 110 while positioning the cap 110 over the sample collection vessel 102. Additionally, or alternatively, the external ridges 125 can be used to rotate and close the sealing cap 110 onto sample collection vessel 102. In some embodiments, ridges 125 may beneficially enable the user to more forcefully torque the sealing cap 110, and the external ridges 125 can provide the user with a better grip during that process. Ridges 125 can also facilitate retraction and/or closure of the selectively openable diaphragm valve 104 and/or removal of the sealing cap 110 at the laboratory when accessing the biological sample, such as manually or by an automated removal mechanism.

Methods Implementing a Solution Cap Having a Selectively Openable Diaphragm Valve With continued reference to FIGS. 1-10, an exemplary method for implementing a multi-part sample collection kit, as described above, includes receiving a biological sample through a funnel connected to the sample collection vessel. The received biological sample can enter directly into the sample collection vessel or by gravitational flow along an interior funnel sidewall. The method can additionally include removing the funnel from the sample collection vessel after facilitating receipt of the biological sample, and associating a sealing cap with the sample collection vessel. The method can additionally include securing the sealing cap (e.g., by rotating the sealing cap 110 along complementary threads between the cap 110 and the vessel 102) to close the cap 110 over the top of the sample collection vessel 102. The sealing cap 110 can contain preservation reagent(s) that are released as the sealing cap 110 is rotated and closed over the sample collection vessel 102. In some embodiments, a selectively openable diaphragm valve 104 associated with the sealing cap 110 undergoes a conformational change when the sealing cap 110 is rotated and closed over the collection vessel 102.

As shown in FIGS. 2 and 3, the solution cap 110 secures to and seals the collection vessel 102 and can do so by any means described herein or as known in the art. In this closed and sealed state, the selectively openable diaphragm valve 104 is in an open configuration, and the reagent(s) mix with the collected sample. The collection vessel 102 can be shaken to allow all or at least most of the preservation reagent to cover the collected sample. Additionally, the biological sample therewithin is beneficially protected from the outside atmosphere by being air- and water-tight. This reduces the chances of the sample contamination and helps maintain the integrity of the probative component during transportation to the laboratory.

In some embodiments, the solution cap is under pressure and moving the selectively openable diaphragm valve into an open position causes the preservation reagent(s) stored within the solution cap to be forcefully expelled into the sample collection chamber. This can beneficially encourage stored reagent(s) to mix with the collected sample and may additionally act to preserve the reagent(s) and/or the probative component thereof.

Methods can additionally include removing the preserved sample from the sample collection system. This can involve, for example, the steps of unscrewing or otherwise removing the solution cap from the sample collection vessel. In doing so, the shim can be retained by the sample collection vessel while the solution cap and associated reagent chamber are drawn away from the sample collection vessel. This can cause the diaphragm valve to reseal (e.g., return to a closed configuration). Further disassociation of the solution cap from the sample collection vessel can cause the diaphragm valve to be removed in a resealed state, exposing the opening of the sample collection vessel and allowing access to the preserved biological sample.

Referring again to FIGS. 1-3, an exemplary use of a sample collection system 100 can include a selectively openable diaphragm valve 104. For example, during assembly of the solution cap 110 with the associated diaphragm valve 104, the reagent chamber 111 of the solution cap can be filled with a measure of sample preservation reagent(s), before or after press-fitting the reagent chamber 111 into the sealing cap 110. As shown in FIGS. 2 and 3, the plug 106 and the shim 108 define a reagent chamber 107 that is in fluid communication with the reagent chamber 111 of the solution cap 110 via a number of fluid vents 130 formed between the plug 106 and the reagent chamber—the plug being coupled to the reagent chamber 111. An upper collar 109 of the reagent chamber 111 extends into—and provides an interference fit with—the reagent chamber 111 of the solution cap 110 (e.g., one or more external protrusions 191 of the reagent chamber 111 form a friction fit with an interior portion of the sealing cap 110).

In the exemplified embodiment, the combination of the plug 106 and shim 108 comprises the selectively openable diaphragm valve 204, which can be selectively and reversibly moved between a sealed configuration 100A and an unsealed configuration 100B. When the shim 108 is associated with the plug 106 and the reagent chamber 111 in the sealed configuration 100A, it can prevent the premature or unintentional expulsion of reagent from the sealing cap 110.

Assembly of the selectively openable diaphragm valve 104 can occur before, during, or after the reagent chamber 111 is attached to the solution cap 110. It can involve advancing the shim 108 over the reagent chamber 111 and associated plug 106 within the solution cap 110 until an exterior-facing guide member 120 on the shim 108 is received (e.g., snap-fittedly received) into a guide channel 116 of the solution cap 110. Once the shim 108 has been advanced over the reagent chamber 111 and the plug 106, forming a fluid-tight seal between the annular diaphragm 161 of the plug and the interior sidewall 122 of the shim 108 and a fluid-tight connection between the exterior sidewall 118 of the reagent chamber 111 and the sealing ring 181, the shim 108 is in an initially sealed configuration 100A, thereby forming reagent retention chamber 107 and obstructing the fluid path between fluid vents 130 and the sample collection chamber 103.

The guide channel 116 of the solution cap 110 can be sized to allow limited translational movement of the guide member 120 within the guide channel 116. This, in turn, restricts the movement of the reagent chamber 111 and the plug 106 relative to the shim 108 when the solution cap 110 is secured and unsecured from the sample collection vessel 102 (e.g., as illustrated in FIGS. 2 and 3 when the solution cap 110 is secured to the sample collection vessel 102, causing the selective unsealing of the selectively openable diaphragm valve 104). An inner facing edge or protrusion of the solution cap 110 can define a lower end of the guide channel 116 and can act to retain the guide member 120 within the guide channel 116, preventing separation of the shim 108 from the solution cap 110 when the solution cap 110 is decoupled from the sample collection vessel 102.

In an exemplary use, the sample collection vessel 102 is used to receive a biological sample through the opening of and into the sample collection vessel 102 (e.g., receiving saliva through an optional funnel temporarily attached to the sample collection vessel 102). After the biological sample is received within the sample collection vessel 102, the user can place the solution cap 110 over the sample collection vessel 102, with the diaphragm valve 104 facing the opening of the sample collection vessel 102 and advance the diaphragm valve 104 into the opening of the sample collection vessel 102. When the diaphragm valve 104 is advanced through the opening of the sample collection vessel 102, the lower collar 132 of the shim 108 becomes friction fit within the upper rim of the sample collection chamber 103. The engagement between the shim 108 and the sample collection chamber 103 can prevent the shim 108 from being advanced further into the sample collection chamber 103 and can prevent the shim 108 from being retracted from the sample collection chamber 103 until the annular diaphragm 161 of the plug 106 has re-formed its seal with the interior sidewall 122 of the shim 108 (as described above).

Alternatively, in other embodiments, a detent 195 formed within the lower collar 132 of the shim 108 can mechanically engage a protruding retention ring (not shown) on the interior sidewall of the sample collection chamber 103. The ring-detent engagement can prevent the shim 108 from being pushed farther into the sample collection vessel 102, but in some variations, the body of the shim 108 above the lower collar 132 abuts an upper rim of the sample collection vessel 102, thereby preventing the shim 108 from being pushed any farther into the sample collection vessel 102.

Further advancement of the solution cap 110 toward the sample collection vessel 102, including engagement of complementary interlocking threads located on the solution cap 110 and the sample collection vessel 102, can force the reagent chamber 111 and the plug 106 through the shim 108 and affect a conformational change in the diaphragm valve 104 from the sealed configuration 100A shown in FIG. 2 to the unsealed configuration 100B shown in FIG. 3. Moving the diaphragm valve 104 from the sealed configuration 100A to the unsealed configuration 100B un-occludes the fluid path between the fluid vents 130 and the sample collection chamber 103 and allows the reagent(s) to flow into the sample collection vessel 102.

The foregoing unsealing of the diaphragm valve can be temporary and reversible. For example, when the solution cap 110 is removed from the sample collection vessel 102 to recover the biological sample, the diaphragm valve 104 can be restored to the sealed configuration 100A, reestablishing the seal between the shim 108 and the plug 106. As the solution cap 110 is unscrewed from the sample collection vessel 102, in some embodiments, the shim 108 can be temporarily retained in a fixed position within the sample collection chamber while the plug 106 and reagent chamber 111 are withdrawn, causing the shim 108 to re-engage with the plug 106 to obstruct the fluid path between the fluid vents 130 and the sample collection chamber 103 (e.g., moving the diaphragm valve 104 from the unsealed configuration 100B of FIG. 3 to the resealed configuration 100A of FIG. 2). The shim 108 can be temporarily retained in the fixed position due to the retention ring within the sample collection vessel 202 mechanically engaging with the detent 195 on the lower collar 132 of the shim 108. With or without a ring-detent structure, the frictional forces between the shim 108 and reagent chamber 111 can be less than the force required to disengage the ring-detent interaction, allowing such relative movement.

When the plug 106 has been withdrawn relative to the sample collection chamber 103 so as to re-engage with the shim 108, the guide member 120 can reach the end of the guide channel 116 where further movement is impeded by the inner facing edge or protrusion of the solution cap 110. The sample collection system 100 is designed, in some embodiments, so that the solution cap 110 and diaphragm valve 104 can—at this point—be removed from the sample collection vessel 202 without the catastrophic failure of any components. That is, the sample collection system 100 can be designed so that the detent 195 on the shim 108 can be disengaged from the protruding ring of the sample collection vessel 202 while maintaining the integrity of the solution cap-diaphragm valve association. This can be enabled, for example, by engineering the components such that the mechanical force required to disengage the ring and detent 195 is less than the force required to remove the guide member 120 from the guide channel 116. Further withdrawal of the solution cap 110 from the sample collection vessel can, therefore, overcome the ring-detent interaction, permitting the solution cap 110, plug 106, and shim 108 to be removed as a single unit from the sample collection vessel 102—with the valve 104 in the resealed configuration 100A.

It should be appreciated that although the foregoing embodiment described the ring being associated with the sample collection vessel 102 and the detent 195 being associated with the shim 108, in some embodiments, the attachment mechanism between the two components may be switched or replaced by other complementary components that perform the same or similar function. For example, the sample collection vessel may include a detent within an interior sidewall that associates with a ring structure disposed on the shim.

Unless defined otherwise, all technical and scientific terms used herein have the same meaning as commonly understood by one of ordinary skill in the art to which the present disclosure pertains.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims.

All changes which come within the meaning and range of equivalency of the claims are to be embraced within their scope.

What is claimed is:

1. A biological sample collection system, comprising:
   a sample collection vessel spanning between a closed first end and a second end having an opening to receive a biological sample into a sample collection chamber defined within the sample collection vessel;
   a sealing cap configured to connect with the second end of the sample collection vessel;
   a reagent chamber configured to secure within an interior space defined by the sealing cap and to retain a measure of sample preservation solution therein;
   a shim configured to circumferentially connect with a proximal end of the reagent chamber and to span a distance between the proximal end of the reagent chamber and an interior sidewall of the sealing cap;
   a plug having a diaphragm sized and shaped to fit within the opening of sample collection vessel and configured to selectively engage the shim and form a seal to retain the measure of sample preservation solution within the reagent chamber,
   wherein connecting the sealing cap with the sample collection vessel displaces the diaphragm from the shim and breaks the seal formed therebetween, opening a fluid path between the reagent chamber and the sample collection chamber,
   wherein the sample collection system comprises a separable two-piece sample collection system that includes (1) the sample collection vessel as a first piece of the separable two-piece sample collection system and (ii) a cap assembly as a second piece of the separable two-piece sample collection system, wherein the cap assembly comprises the sealing cap, the reagent chamber secured within the interior space of the sealing cap, the shim circumferentially connected with the proximal end of the reagent chamber and spanning the distance between the proximal end of the reagent chamber and the interior sidewall of the sealing cap, and the plug, the plug engaging the shim and sealing the measure of sample preservation solution within the reagent chamber,
   wherein the plug additionally comprises a plug body, the plug body configured to insert within an interior portion of the proximal end of the reagent chamber, and
   wherein the interior portion of the proximal end of the reagent chamber comprises one or more protrusions extending therefrom that are configured to engage the plug body and form a space between an outer sidewall of the plug body and an interior sidewall of the proximal end of the reagent chamber.

2. The biological sample collection system as in claim 1, wherein the sample collection vessel further comprises a connection member and the sealing cap comprises a complementary connection member configured to connect with the connection member of the sample collection vessel and to couple the sample collection vessel and the sealing cap.

3. The biological sample collection system as in claim 2, wherein the connection member comprises a ridge projecting away from the sample collection vessel or a depression within the sample collection vessel and the complementary connection member comprises a hook or ridge sized and shaped to engage the connection member.

4. The biological sample collection system as in claim 2, wherein the connection member and the complementary connection member comprise interlocking threads.

5. The biological sample collection system as in claim 1, wherein the reagent chamber additionally comprises a connection element configured to abut the plug body and to break the seal between the diaphragm and the shim.

6. The biological sample collection system as in claim 1, wherein the space comprises a portion of the fluid path that permits the measure of sample preservation solution to pass around the outer sidewall of the plug body, and when the seal is broken between the diaphragm and the shim, around the diaphragm.

7. The biological sample collection system as in claim 1, wherein the shim additionally comprises a guide member sized and shaped to be received by a guide channel of the sealing cap.

8. The biological sample collection system as in claim 1, wherein the shim includes a sealing protrusion configured to form a fluid-tight connection between the shim and the proximal end of the reagent chamber, and a sample collection chamber sealing surface that forms a fluid-tight seal between the shim and the opening of the sample collection chamber when the sealing cap is connected with the sample collection vessel.

9. The biological sample collection system as in claim 1, wherein the diaphragm of the plug comprises an annular diaphragm spatially offset from a bottom opening of the reagent chamber and engaging the shim.

10. The biological sample collection system as in claim 9, wherein the fluid path between the reagent chamber and the sample collection chamber is obstructed by the shim and the annular diaphragm when the plug is engaged with the shim, and wherein the fluid path is unobstructed when the plug is disengaged from the shim by connecting the sealing cap with the sample collection vessel.

11. The biological sample collection system as in claim 1, wherein the reagent chamber comprises a retaining ring configured to secure the reagent chamber with a reagent chamber connection member disposed within the interior space of the sealing cap.

12. The biological sample collection system as in claim 11, wherein the reagent chamber connection member comprises a sidewall protrusion sized and shaped to retain the reagent chamber in connection with the sealing cap.

13. A biological sample collection system, comprising:
a sample collection vessel spanning between a closed first end and a second end having an opening to receive a biological sample into a sample collection chamber defined within the sample collection vessel;
a sealing cap configured to connect with the second end of the sample collection vessel;
a reagent chamber configured to secure within an interior space defined by the sealing cap and to retain a measure of sample preservation solution therein;
shim configured to circumferentially connect with a proximal end of the reagent chamber and to span a distance between the proximal end of the reagent chamber and an interior sidewall of the sealing cap;
a plug having a diaphragm sized and shaped to fit within the opening of sample collection vessel and configured to selectively engage the shim and form a seal to retain the measure of sample preservation solution within the reagent chamber,
wherein connecting the sealing cap with the sample collection vessel displaces the diaphragm from the shim and breaks the seal formed therebetween, opening a fluid path between the reagent chamber and the sample collection chamber,
wherein the sample collection system comprises a separable two-piece sample collection system that includes (1) the sample collection vessel as a first piece of the separable two-piece sample collection system and (ii) a cap assembly as a second piece of the separable two-piece sample collection system, wherein the cap assembly comprises the sealing cap, the reagent chamber secured within the interior space of the sealing cap, the shim circumferentially connected with the proximal end of the reagent chamber and spanning the distance between the proximal end of the reagent chamber and the interior sidewall of the sealing cap, and the plug, the plug engaging the shim and sealing the measure of sample preservation solution within the reagent chamber, and
wherein the shim includes a sealing protrusion configured to form a fluid-tight connection between the shim and the proximal end of the reagent chamber, and a sample collection chamber sealing surface that forms a fluid-tight seal between the shim and the opening of the sample collection chamber when the sealing cap is connected with the sample collection vessel.

14. The biological sample collection system as in claim 13, wherein the sealing protrusion is a sealing ring that extends inward from an interior sidewall of the shim.

15. The biological sample collection system as in claim 13, wherein the sealing protrusion is a sealing ring that is composed of an elastic material.

16. The biological sample collection system as in claim 13, wherein the sealing protrusion is configured to contact an exterior sidewall of the reagent chamber to form a fluid-tight seal between the interior sidewall of the shim and the exterior sidewall of the reagent chamber.

17. A biological sample collection system, comprising:
a sample collection vessel spanning between a closed first end and a second end having an opening to receive a biological sample into a sample collection chamber defined within the sample collection vessel;
a sealing cap configured to connect with the second end of the sample collection vessel;
a reagent chamber configured to secure within an interior space defined by the sealing cap and to retain a measure of sample preservation solution therein;
a shim configured to circumferentially connect with a proximal end of the reagent chamber and to span a distance between the proximal end of the reagent chamber and an interior sidewall of the sealing cap;
a plug having a diaphragm sized and shaped to fit within the opening of sample collection vessel and configured to selectively engage the shim and form a seal to retain the measure of sample preservation solution within the reagent chamber,
wherein connecting the sealing cap with the sample collection vessel displaces the diaphragm from the shim and breaks the seal formed therebetween, opening a fluid path between the reagent chamber and the sample collection chamber,
wherein an interior portion of the proximal end of the reagent chamber comprises one or more protrusions extending therefrom that are configured to engage the plug and form a space between an outer sidewall of the plug and an interior sidewall of the proximal end of the reagent chamber.

18. The biological sample collection system as in claim 17, wherein the plug comprises a plug body, the plug body being configured to be inserted within an interior portion of the proximal end of the reagent chamber such that the one or more protrusions extending from the interior portion of the proximal end of the reagent chamber engage the plug body.

19. A biological sample collection system, comprising:
- a sample collection vessel spanning between a closed first end and a second end having an opening to receive a biological sample into a sample collection chamber defined within the sample collection vessel;
- a sealing cap configured to connect with the second end of the sample collection vessel;
- a reagent chamber configured to secure within an interior space defined by the sealing cap and to retain a measure of sample preservation solution therein;
- a shim configured to circumferentially connect with a proximal end of the reagent chamber and to span a distance between the proximal end of the reagent chamber and an interior sidewall of the sealing cap;
- a plug having a diaphragm sized and shaped to fit within the opening of sample collection vessel and configured to selectively engage the shim and form a seal to retain the measure of sample preservation solution within the reagent chamber, wherein connecting the sealing cap with the sample collection vessel displaces the diaphragm from the shim and breaks the seal formed therebetween, opening a fluid path between the reagent chamber and the sample collection chamber, wherein the shim includes a sealing protrusion configured to form a fluid-tight connection between the shim and the proximal end of the reagent chamber, and a sample collection chamber sealing surface that forms a fluid-tight seal between the shim and the opening of the sample collection chamber when the sealing cap is connected with the sample collection vessel.

* * * * *